US009993581B2

(12) United States Patent
Phillips et al.

(10) Patent No.: US 9,993,581 B2
(45) Date of Patent: Jun. 12, 2018

(54) ENGINEERED NEURAL TISSUE

(71) Applicant: The Open University, Milton Keynes (GB)

(72) Inventors: James Phillips, Milton Keynes (GB); Melanie Georgiou, Milton Keynes (GB)

(73) Assignee: UCL Business PLC (GB)

( * ) Notice: Subject to any disclaimer, the term of this patent is extended or adjusted under 35 U.S.C. 154(b) by 0 days. days.

(21) Appl. No.: 14/908,860

(22) PCT Filed: Jul. 29, 2014

(86) PCT No.: PCT/GB2014/052318
§ 371 (c)(1),
(2) Date: Jan. 29, 2016

(87) PCT Pub. No.: WO2015/015185
PCT Pub. Date: Feb. 5, 2015

(65) Prior Publication Data
US 2016/0166733 A1 Jun. 16, 2016

(30) Foreign Application Priority Data
Jul. 31, 2013 (GB) .................................. 1313704.7

(51) Int. Cl.
| | |
|---|---|
| *A61L 27/38* | (2006.01) |
| *A61K 35/30* | (2015.01) |
| *C12N 5/079* | (2010.01) |
| *C12N 5/0797* | (2010.01) |
| *A61L 27/24* | (2006.01) |
| *A61L 27/36* | (2006.01) |
| *A61L 27/52* | (2006.01) |
| *A61L 27/54* | (2006.01) |
| *A61K 35/12* | (2015.01) |

(52) U.S. Cl.
CPC ............ *A61L 27/383* (2013.01); *A61K 35/30* (2013.01); *A61L 27/24* (2013.01); *A61L 27/3691* (2013.01); *A61L 27/3878* (2013.01); *A61L 27/52* (2013.01); *A61L 27/54* (2013.01); *C12N 5/0622* (2013.01); *C12N 5/0623* (2013.01); *A61K 35/12* (2013.01); *A61L 2300/412* (2013.01); *A61L 2300/62* (2013.01); *A61L 2300/64* (2013.01); *A61L 2430/32* (2013.01); *C12N 2501/06* (2013.01); *C12N 2501/11* (2013.01); *C12N 2501/115* (2013.01); *C12N 2533/54* (2013.01)

(58) Field of Classification Search
None
See application file for complete search history.

(56) References Cited

FOREIGN PATENT DOCUMENTS

WO   WO 2004/087231 A1   10/2004

OTHER PUBLICATIONS

Phillips et al., Tissue Engineering, 11(9/10): 1611-1617, 2005.*
Serpooshan et al., J Biomed Mat Res A, vol. 96A, Issue 4:609-620, Mar. 2011.*
Liang et al., Biomaterials, 34:5521-5529, published online Apr. 25, 2013.*
International Search Report and Written Opinion for Application No. PCT/GB2014/052318 dated Nov. 21, 2014.
International Preliminary Report on Patentability for Application No. PCT/GB2014/052318 dated Feb. 11, 2016.
East et al., A 3D in vitro model reveals differences in the astrocyte response elicited by potential stem cell therapies for CNS injury. Regen Med. Nov. 2013;8(6):739-46. doi: 10.2217/rme.13.61.
Georgiou et al., Engineered neural tissue for peripheral nerve repair. Biomaterials. Oct. 2013;34(30):7335-43. doi: 10.1016/j.biomaterials.2013.06.025. Epub Jul. 5, 2013.
Liang et al., The survival of engrafted neural stem cells within hyaluronic acid hydrogels. Biomaterials. Jul. 2013;34(22):5521-9. doi: 10.1016/j.biomaterials.2013.03.095. Epub Apr. 25, 2013.
Martens et al., Human dental pulp stem cells can differentiate into Schwann cells and promote and guide neurite outgrowth in an aligned tissue-engineered collagen construct in vitro. FASEB J. Apr. 2014;28(4):1634-43. doi: 10.1096/fj.13-243980. Epub Dec. 18, 2013.
Sanen et al., Aligned Schwann cells derived from human dental pulp stem cells direct neurite growth in a tissue engineered collagen construct. GLIA. Jun. 2013; 61(1): S196.
Tong et al., Differentiation of neural stem cells into Schwann-like cells in vitro. Biochem Biophys Res Commun. Oct. 29, 2010;401(4):592-7. doi: 10.1016/j.bbrc.2010.09.107. Epub Oct. 20, 2010.

* cited by examiner

Primary Examiner — Kimberly Ballard
Assistant Examiner — Stacey N MacFarlane
(74) Attorney, Agent, or Firm — Wolf, Greenfield & Sacks, P.C.

(57) ABSTRACT

A method for producing an engineered tissue scaffold for neural repair is described. The method includes tethering a hydrogel matrix seeded with tension-generating cells to a frame, and allowing the tension-generating cells to generate tension within the matrix, such that the cells self-align. The matrix may then be at least partially dehydrated to form a sheet. The tension-generating cells are stem cells capable of differentiating into cells having Schwann-cell-like properties, or are derived from such stem cells. In preferred embodiments, the cells are neural stem cells, for example conditionally immortalized neural stem cells of fetal cortex origin.

9 Claims, 3 Drawing Sheets

Figure 1
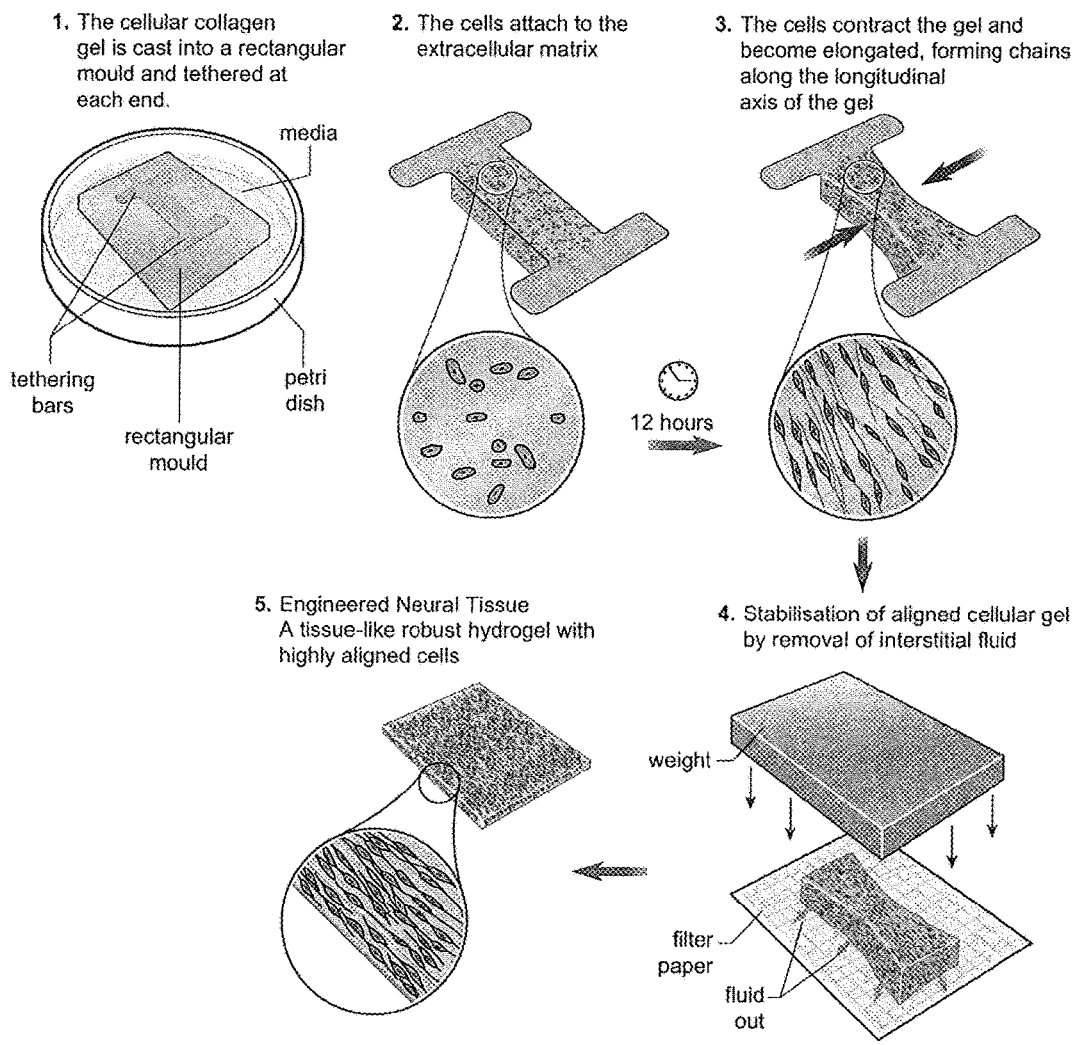
(from Georgiou et al, 2013)
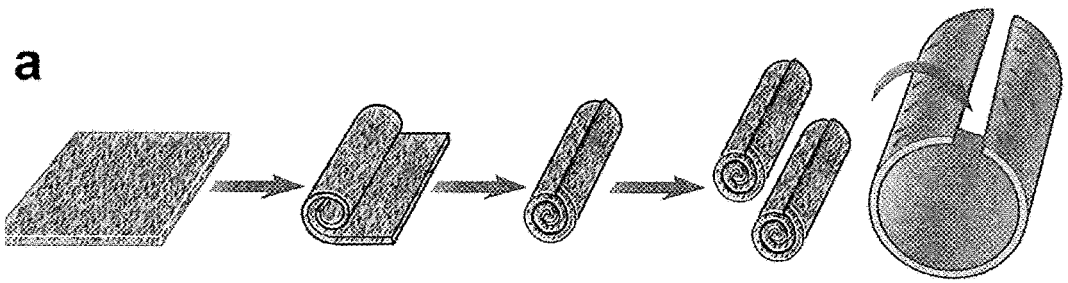
Figure 2 (from Georgiou et al)

ENGINEERED NEURAL TISSUE

RELATED APPLICATIONS

This application is a national stage filing under 35 U.S.C. § 371 of international application PCT/GB2014/052318, filed Jul. 29, 2014, which claims priority to United Kingdom Patent Application No. 1313704.7, filed Jul. 31, 2013. The contents of this international application are incorporated by reference herein in their entirety.

FIELD OF THE INVENTION

The present invention relates to a method and apparatus for producing engineered neural tissue, for use in nerve repair of human and animal subjects.

BACKGROUND TO THE INVENTION

Nerve damage in patients will often not regenerate naturally, and can lead to permanent loss of sensitivity and function. For this reason, surgical and therapeutic interventions to promote repair can be desirable.

International patent application WO2004/087231 describes a self-aligning tissue growth guide. The guide comprises a core of a biopolymer matrix which is fixed to an outer sheath at two points. The core is seeded with cells, which generate a mechanical contractile force leading to self-alignment of the cells within the core. This produces a cellular guidance substrate for regenerating tissue in vivo. The tension in the core can also lead the fibres of the matrix to align. The combination of cellular alignment and substrate alignment serves to guide cellular regrowth in a subject.

As described in WO2004/087231, the biopolymer matrix is preferably a collagen matrix. Cells used to seed the matrix align and contract but do not proliferate to form organised tissue. The list of cells given in the publication as being of use includes Schwann cells. An embodiment of the guide may also include cells from the tissue of interest seeded within the matrix, and which will grow and be guided by the contractile cells.

The guide as described in this publication needs to remain tethered within the sheath in order to retain tension and alignment of the cells. This reduces the utility and versatility of the device.

Georgiou et al, "Engineered neural tissue for peripheral nerve repair", Biomaterials 34 (2013) 7335-7343 describe an alternative technique in which sheets of matrix are prepared which are tethered to a mould. Seeding the matrix with Schwann cells leads to tension generation and cell self-alignment. The matrix is then removed from the mould, and partially dehydrated by removal of interstitial fluid. This results in a more robust sheet of anisotropic matrix seeded with Schwann cells. The sheet can be rolled into rods and implanted in experimental subjects to assess neural regrowth. The authors conclude that the rods are able to promote neural regrowth, and that the presence of live Schwann cells is important for clinical activity.

However, a major barrier to putting this into the clinic is to identify an available source of suitable cells. There is no suitable source of human Schwann cells. Stem cells from bone marrow or adipose tissue may be differentiated into cells with characteristics similar to Schwann cells, but there are challenges with clinical delivery, there may be a need for tissue matching, (allogeneic nerve autografts are known to provoke immune response and rejection). Use of autologous cells would involve much more complex processing, with logistical issues (cell shipping for processing, patient availability for cell harvest and return) and a high cost of goods to expand and differentiate individual patient's cells. It would be desirable to provide a technique using an alternate source of cells, preferably one with similar efficacy to Schwann cells.

BRIEF SUMMARY OF THE INVENTION

According to a first aspect of the present invention, there is provided a method for producing an engineered tissue scaffold for neural repair, the method comprising:
  i) providing a cell guide comprising a hydrogel matrix seeded with tension-generating cells, the matrix being tethered at opposed first and second ends to a frame;
  ii) allowing the tension-generating cells to generate tension within the matrix, such that the cells self-align within the matrix; and
  iii) removing liquid from the hydrogel matrix in order to at least partially dehydrate the matrix to form a sheet while retaining cells within the matrix;
thereby providing an engineered tissue scaffold, wherein the tension-generating cells are not Schwann cells, but are stem cells capable of differentiating into cells having Schwann-cell-like properties, or are derived from such stem cells.

By Schwann-cell-like properties is meant that the cells show a phenotypic characteristic also showed by Schwann cells. A preferred such characteristic is the ability to maintain neurons alive when present in the matrix.

In a preferred embodiment, the cells are a therapeutic cell type (that is, suitable for, and/or approved for, use in therapy). In certain embodiments, the matrix is seeded with stem cells, preferably neural stem cells, for example the ReNcell CX line (Merck Millipore Ltd). Particularly preferred neural stem cells are the CTX0E03 neural stem cell line (CTX), produced by ReNeuron Group plc, United Kingdom. These cells are conditionally immortalised neural stem cells of fetal cortex origin, and their generation and maintenance is described in EP 1 645 626. Cells as described in this publication are particularly preferred for use in the present invention, having already been used in clinical trials (NCT01151124, clinicaltrials.gov), but other neural stem cells may also be used. The neural stem cells used in the invention can be a fetal, an embryonic, or an adult neural stem cell, such as has been described in U.S. Pat. Nos. 5,851,832, 6,777,233, 6,468,794, 5,753,506 and WO-A-2005121318. The fetal tissue may be human fetal cortex tissue. The cells can be selected as neural stem cells from the differentiation of induced pluripotent stem (iPS) cells, as has been described by Yuan et al. (2011) or a directly induced neural stem cell produced from somatic cells such as fibroblasts (for example by constitutively inducing Sox2, Klf4, and c-Myc while strictly limiting Oct4 activity to the initial phase of reprogramming as described recently by Their et al, 2012). Human embryonic stem cells may be obtained by methods that preserve the viability of the donor embryo, as is known in the art (e.g. Klimanskaya et al., 2006, and Chung et al. 2008). Other stable neural stem cell lines may be used. The cells may be conditionally immortalised, as with CTX cells.

In certain embodiments, the matrix is seeded with non-neural stem cells having the ability to differentiate into cells having Schwann-cell-like properties. One example of such cells is mesenchymal stem cells.

Although in preferred embodiments of the invention, the cells are stem cells, in other embodiments, the cells used may be cells derived from such stem cells as described, for example, by differentiation of such stem cells.

In certain embodiments of the invention, the cells may be autologous cells harvested from the patient, but this is not preferred; in preferred embodiments, the cells are heterologous. The use of neural stem cells reduces problems otherwise associated with use of heterologous differentiated cells.

The method may comprise, as step i), the steps of i)a) providing a cell guide comprising a hydrogel matrix, and i)b) seeding the matrix with tension-generating cells.

The step of allowing the tension-generating cells to generate tension within the matrix may comprise the step of allowing the cells to differentiate within the matrix. This is particularly applicable to the use of neural stem cells within the matrix. It is believed that stem cells will differentiate within the matrix as a consequence of cell interaction with the matrix, and/or the withdrawal of growth factors and signals present in the medium used to maintain the cells in culture prior to their introduction into the matrix. However, in certain embodiments, the cells may be caused to differentiate by the addition of specific growth factors or signals to the matrix. Such signals and factors will depend on the cell type used, and will be known to the skilled person. In other embodiments, the cells may be caused to differentiate prior to their introduction into the matrix.

The method may further comprise the step of removing the matrix from the frame, between steps ii) and iii).

The hydrogel matrix is preferably a biopolymer hydrogel matrix, more preferably a collagen matrix, and most preferably a type I collagen matrix. Alternatively, a fibrin matrix may be used. Other suitable matrix materials are given in WO2004/087231, and include fibronectin, gelatin, and biosorbable polymers such as polylactide, polyglycolic acid, and polycapryolactone.

The step of removing liquid from the hydrogel matrix may comprise contacting the matrix with an absorbent material. The material may be, for example, an absorbent paper. The removal step may also comprise applying pressure to the matrix and/or absorbent material. Suitable methods for removing liquid from the matrix to create tissue equivalents are described in European patent 1 773 416 and equivalents. Porous absorbers which may be used in such methods are described in European patent application 2 580 313 and equivalents.

The frame may be a sheath surrounding the matrix, but preferably the frame is in the form of a mould; this allows the hydrogel matrix to be poured and cast directly within the frame. Any suitable material may be used for the mould; for example, plastic.

The method may further comprise the step of iv) forming the sheet into a rod shape. The step of forming the sheet into a rod may comprise rolling the sheet, or a portion of the sheet, to form a rod. The rod may be cut to size. A single sheet may be used to form a plurality of rods. The use of rods mimics the natural organisation of nerves and neural tissue more closely than does sheets of non-dehydrated hydrogel materials.

The method may further comprise the step of encapsulating one or more sheets, portions of sheets, or rods in an outer sheath. The outer sheath may be a collagen matrix; in preferred embodiments, the outer sheath is the same material as the hydrogel matrix. The outer sheath is preferably an at least partially dehydrated matrix without cells seeded within it. This provides a non-aligned matrix which is biocompatible.

The method may still further comprise the step of freezing the engineered tissue scaffold. Freezing may be done in liquid nitrogen, or in equivalent temperatures. This allows preservation of the prepared matrix, with minimal cell death.

The method may further comprise the step of implanting the engineered tissue scaffold into a patient. The patient may be human, or may be an animal, preferably a mammal. The patient may have damaged neural tissue, particularly in the peripheral nervous system. Alternatively, the damaged neural tissue may be in the central nervous system. The scaffold may be implanted at the site of tissue damage, for example, across a gap within a nerve.

According to a further aspect of the invention, there is provided an engineered tissue growth guide for neuronal regeneration, the guide comprising one or more sheets of at least partially dehydrated aligned matrix material, the matrix being seeded with tension generating cells which are not Schwann cells, but are stem cells capable of differentiating into cells having Schwann-cell-like properties, or are derived from such stem cells.

In a preferred embodiment, the cells are a therapeutic cell type (that is, suitable for, and/or approved for, use in therapy). In certain embodiments, the matrix is seeded with stem cells, preferably neural stem cells, for example the ReNcell CX line (Merck Millipore Ltd). Particularly preferred neural stem cells are the CTX0E03 neural stem cell line (CTX), produced by ReNeuron Group plc, United Kingdom. These cells are conditionally immortalised neural stem cells of fetal cortex origin, and their generation and maintenance is described in EP 1 645 626. Cells as described in this publication are particularly preferred for use in the present invention, having already been used in clinical trials (NCT01151124, clinicaltrials.gov), but other neural stem cells may also be used. The neural stem cells used in the invention can be a fetal, an embryonic, or an adult neural stem cell, such as has been described in U.S. Pat. Nos. 5,851,832, 6,777,233, 6,468,794, 5,753,506 and WO-A-2005121318. The fetal tissue may be human fetal cortex tissue. The cells can be selected as neural stem cells from the differentiation of induced pluripotent stem (iPS) cells, as has been described by Yuan et al. (2011) or a directly induced neural stem cell produced from somatic cells such as fibroblasts (for example by constitutively inducing Sox2, Klf4, and c-Myc while strictly limiting Oct4 activity to the initial phase of reprogramming as described recently by Their et al, 2012). Human embryonic stem cells may be obtained by methods that preserve the viability of the donor embryo, as is known in the art (e.g. Klimanskaya et al., 2006, and Chung et al. 2008). Other stable neural stem cell lines may be used. The cells may be conditionally immortalised, as with CTX cells.

In certain embodiments, the matrix is seeded with non-neural stem cells having the ability to differentiate into cells having Schwann-cell-like properties. One example of such cells is mesenchymal stem cells.

Although in preferred embodiments of the invention, the cells are stem cells, in other embodiments, the cells used may be cells derived from such stem cells as described, for example, by differentiation of such stem cells.

Where neural stem cells are used in the invention, preferably the cells have been allowed to differentiate within the matrix.

The hydrogel matrix is preferably a biopolymer hydrogel matrix, more preferably a collagen matrix, and most preferably a type I collagen matrix.

The sheets may be formed into rods, for example by rolling a sheet of matrix material into a rod shape.

The guide may comprise a plurality of sheets or rods.

The guide may further comprise an outer sheath encapsulating the one or more sheets and/or rods. The outer sheath may be a collagen matrix; in preferred embodiments, the outer sheath is the same material as the hydrogel matrix. The outer sheath is preferably an at least partially dehydrated matrix without cells seeded within it.

Preferably the guide is for repair of the peripheral nervous system. However, it is believed that the guide is also suitable for repair of the central nervous system.

Also provided according to the present invention is a kit comprising one or more engineered neural tissue sheets of at least partially dehydrated aligned matrix material, the matrix being seeded with tension generating cells which are not Schwann cells, but are stem cells capable of differentiating into cells having Schwann-cell-like properties, or are derived from such stem cells; and one or more outer sheaths, each sheath being formed from a sheet of at least partially dehydrated matrix material without cells seeded within.

The sheets may be formed into one or more rods, for example by rolling a sheet into a rod-like form.

In a preferred embodiment, the cells are a therapeutic cell type (that is, suitable for, and/or approved for, use in therapy). In certain embodiments, the matrix is seeded with stem cells, preferably neural stem cells, for example the ReNcell CX line (Merck Millipore Ltd). Particularly preferred neural stem cells are the CTX0E03 neural stem cell line (CTX), produced by ReNeuron Group plc, United Kingdom. These cells are conditionally immortalised neural stem cells of fetal cortex origin, and their generation and maintenance is described in EP 1 645 626. Cells as described in this publication are particularly preferred for use in the present invention, having already been used in clinical trials (NCT01151124, clinicaltrials.gov), but other neural stem cells may also be used. The neural stem cells used in the invention can be a fetal, an embryonic, or an adult neural stem cell, such as has been described in U.S. Pat. Nos. 5,851,832, 6,777,233, 6,468,794, 5,753,506 and WO-A-2005121318. The fetal tissue may be human fetal cortex tissue. The cells can be selected as neural stem cells from the differentiation of induced pluripotent stem (iPS) cells, as has been described by Yuan et al. (2011) or a directly induced neural stem cell produced from somatic cells such as fibroblasts (for example by constitutively inducing Sox2, Klf4, and c-Myc while strictly limiting Oct4 activity to the initial phase of reprogramming as described recently by Their et al, 2012). Human embryonic stem cells may be obtained by methods that preserve the viability of the donor embryo, as is known in the art (e.g. Klimanskaya et al., 2006, and Chung et al. 2008). Other stable neural stem cell lines may be used. The cells may be conditionally immortalised, as with CTX cells.

In certain embodiments, the matrix is seeded with non-neural stem cells having the ability to differentiate into cells having Schwann-cell-like properties. One example of such cells is mesenchymal stem cells.

Although in preferred embodiments of the invention, the cells are stem cells, in other embodiments, the cells used may be cells derived from such stem cells as described, for example, by differentiation of such stem cells.

A still further aspect of the invention provides a method for promoting regrowth and/or repair of damaged neural tissue, the method comprising implanting an engineered tissue scaffold as described herein into a patient having damaged neural tissue. The patient may be human, or may be an animal, preferably a mammal. The scaffold may be implanted at the site of tissue damage, for example, across a gap within a nerve. Preferably the damaged neural tissue is in the peripheral nervous system. Alternatively, the damaged neural tissue may be in the central nervous system.

BRIEF DESCRIPTION OF THE DRAWINGS

FIG. 1 shows a schematic diagram of several stages in the production of tissue guides in accordance with the invention.

FIG. 2 shows an illustration of forming rolled rods and encapsulation in an outer sheath.

DETAILED DESCRIPTION OF THE INVENTION

Stem Cells and Neural Cells

Figure 3:
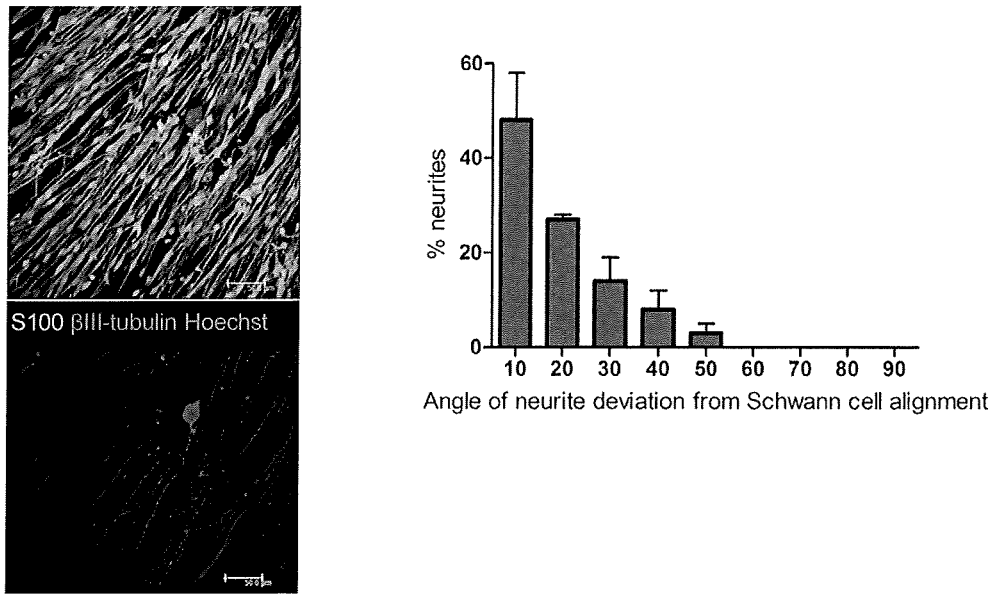
FIG. 3 shows the results of Experiment 1. EngNT containing Schwann cells supports and directs neuronal growth in vitro. Regenerating adult rat dorsal root ganglion neurites follow the Schwann cell alignment present within EngNT (confocal micrographs of the same field showing neurons (red) after 3 days in co-culture with EngNT sheets formed using a rat Schwann cell line (green), scale bar 50 µm). The graph shows that a very high degree of alignment is achieved.

The term "stem cell" is used herein to refer to cell types which have the ability to self-renew to produce more stem cells, and to differentiate into other cell types. The term "neural cells" refers to cells having at least an indication of neuronal or glial phenotype, such as staining for one or more neuronal or glial markers or which will differentiate into cells exhibiting neuronal or glial markers. Examples of neuronal markers which may be used to identify neuronal cells include, for example, neuron-specific nuclear protein, tyrosine hydroxylase, microtubule associated protein, and calbindin, among others. The term neural cells also includes cells which are neural precursor cells, i.e., stem cells which will differentiate into or become neural cells or cells which will ultimately exhibit neuronal or glial markers, such term including pluripotent stem cells which ultimately differentiate into neuronal and/or glial cells. All of the above cells and their progeny are construed as neural cells for the purpose of the present invention. Neural stem cells give rise to neurons, astrocytes and oligodendrocytes during development and can replace a number of neural cells in the adult brain. Neural stem cells are neural cells for purposes of the present invention.

Peripheral Nerve Injury and Repair

Peripheral nerves convey sensory signals from the body to the Central Nervous System (CNS) and motor signals from the CNS to the muscles. They contain bundles of axons (the long cellular processes of neurons that convey the nerve signals), each of which is supported by columns of Schwann cells within an extracellular matrix of longitudinally aligned collagen fibrils. Peripheral Nervous System (PNS) neurons have their cell bodies (containing the nucleus) in or near the spinal cord. This means that when an axon is severed, the distal part that is separated from the cell body disintegrates, but the proximal part that remains attached can sometimes survive. This part may be able to extend again, and if the regenerating axon reaches the degenerating nerve segment beyond the injury it can grow (at ~1 mm per day) in the supportive environment formed by the remaining Schwann cell columns and collagen architecture. Surgery to re-join the severed nerve stumps directly is the best hope of successful repair, but where this would create too much tension the gap must be bridged. Short gaps (<30 mm) can be repaired with a simple tube—this supports formation of a fibrin tissue bridge that becomes populated with Schwann cells from the stumps and supports neuronal regeneration. However, this becomes inadequate for gaps >30 mm which are currently repaired using an autograft; a piece of healthy harvested from the patient. The original axons within the graft degenerate leaving columns of Schwann cells and an aligned collagen tissue structure to provide the trophic support and cell-level guidance required to support regeneration at the repair site. The present invention recreates the key cellular and extracellular features of nerve tissue grafts and can be used in place of host nerve to repair long gaps.

Causes of Peripheral Nerve Injury

The main causes of peripheral nerve injury (PNI) are trauma, from accidents, fractures, lacerations and wounding, or as a result of surgery, i.e. to remove a tumour, and from compression syndrome. Estimates of incidence are that 3-5% of all trauma cases will lead to PNI, and that this may affect up to 1 million people annually in the US and Europe. According to Belkas (2004), many PNI injuries result in life-long disability; in the United States alone, 360,000 people suffer from upper extremity paralytic syndromes on an annual basis, resulting in over 8.5 million restricted activity days and almost 5 million bed/disability days. In a study (Noble 1998) of 1 year at a US regional trauma centre, in which 5,700 patients were treated, 2.8% suffered PNI, 46% of injuries resulted from a car crash, the radial nerve, or other upper extremity, was most often involved and some patients suffered injuries to more than one nerve. The mean patient age was 34 years.

An important cause of PNI is during surgery to remove a tumour, which can cause major side effects. For example, the American Cancer Society estimates 238,000 US men are diagnosed annually with prostate cancer, and it will afflict one man in six during his lifetime. Almost a third of patients have a radical prostatectomy, removal of the cancerous organ, during which nerve injury can occur, leading to erectile dysfunction.

However the incidence of PNI is thought to be "grossly underestimated" due to the range of causes, and number of clinical disciplines that may be involved, (Pfister 2011). The consequence of severe PNI is that the individual suffers from pain, loss of sensation and muscle strength, reducing dexterity and affecting quality of life, or in severe case the muscle may lose motor function completely, leading to disability. A Swedish study showed that forearm PNI patients average 273 sick days (Rosberg 2005) and "the cost to society for a median nerve injury in the forearm may exceed € 50,000" (Dahlin 2008). Accidents disproportionally affect younger males, so the impact of their reduced economic activity over a lifetime is significant.

Treatment options for PNI will depend on the site and severity of the injury; they range from surgery to join severed nerve ends where there is no gap, to the use of wraps as a nerve guide or conduit to bridge shorter gaps. Four absorbable conduits (from Integra LifeSciences, Polyganics, Synovis Micro Companies Alliance Inc. and Collagen Matrix Inc.), involving 3 materials (collagen, polycaprolactone and polyglycolic acid) have obtained US FDA and CE approval for clinical use. These are empty tubes which function by providing a conduit for overall tissue guidance and containment, to concentrate factors and reduce fibrosis/adhesion. Injuries that result in a gap greater than 30 mm may be treated with the nerve autograft. A healthy nerve is harvested, most frequently the sural nerve from the leg, and used to join the nerve ends. Nerve harvest necessitates an additional procedure; it may require a specialist plastic surgeon and be performed separately from the trauma surgery, with consequent additional time and cost. Nerve harvest causes damage at the donor site, leading to loss of sensation and sometime neuropathic pain. Autograft outcomes may be poor or variable as there may insufficient nerve length or number of fascicles to be a good match for the injury. AxoGen is the first company to develop a product for the long-gap market: Avance® Nerve Graft, which is a decellularized and sterile extracellular matrix processed from human peripheral nerve tissue, it is available in different lengths and can be used to bridge gaps up to 70 mm in length. Avance® functions include those of the nerve wraps, and in addition provide an intraluminal structure with the correct tissue architecture.

EXAMPLES

FIG. 1 shows a schematic diagram of several stages in the production of tissue guides in accordance with the invention.

Cells are maintained in culture according to the manufacturer's instructions. For undifferentiated CX cells the media was supplemented with EGF (20 ng/ml working concentration) and FGF-2 (20 ng/ml). For the undifferentiated CTX cells the media was supplemented with tamoxifen (1 µl per 10 ml of media), EGF (20 ng/ml) and FGF-2 (10 ng/ml). The differentiation protocol for the CX cells was the removal of EGF and FGF, the differentiation protocol for the CTX cells was the removal of EGF, FGF-2 and tamoxifen. The protocols for the differentiation of CX and CTX were both over a 2 week period.

Cells are aligned within tethered collagen gels in rectangular stainless steel moulds, before stabilisation by plastic compression. To prepare gels, 1 volume of 10× minimum essential medium (Sigma) was mixed with 8 volumes of type I rat tail collagen (2 mg/ml in 0.6% acetic acid; First Link, UK) and the mixture neutralised using sodium hydroxide before addition of 1 volume of cell suspension (final density $4 \times 10^6$ cells per ml of gel). One ml of this mixture was added to each mould at 4 deg C. and integrated with tethering mesh at opposite ends before setting at 37 deg C. for 10 min. Tethered gels were immersed in culture medium and incubated at 37 deg C. in a humidified incubator with 5% CO2/95% air for 24 h to allow alignment to develop. Aligned cellular gels were stabilised by plastic compression (in accordance with the method described in European patent 1 773 416). The plastic compression parameters used here were selected to ensure stabilisation was rapid, sufficient to retain cellular alignment in the absence of tethering, and caused minimal cell death. Aligned tethered gels were separated from the tethering mesh using a scalpel, placed on an absorbent paper pad and immediately compressed by loading the gel with 120 g for 1 min during which time fluid was absorbed by the paper pad underneath. The resulting sheets were either transferred directly to 24-well plates for in vitro experiments, or rolled to form rods (approximately 200 mm diameter×15 mm length), and maintained in culture medium for up to 24 h prior to in vivo experiments. See FIG. 2 for an illustration of forming rolled rods and encapsulation in an outer sheath. The outer sheath is formed in the same way as the sheets, but without the inclusion of cells.

To test efficacy in vivo a rat model of peripheral nerve repair is used. Sprague Dawley rats were deeply anesthetised by inhalation of isoflurane. The left sciatic nerve of each animal was exposed at mid-thigh and transected. Aligned rolled cell sheets are placed in a commercially available wrap, NeuraWrap™, and sutured into place in a 15 mm gap, and the repair is monitored after 8 weeks. Conduits were retained in place using three 10/0 epineurial sutures at each stump, then wounds were closed in layers and animals were allowed to recover. The results of initial in vitro and in vivo experiments are very promising; aligned Schwann cells both support the outgrowth of neurites and direct neuronal growth, see experiments 1 and 2.

Experiment 1

EngNT Containing Schwann Cells Supports and Directs Neuronal Growth In Vitro

Results shown in FIG. 3. Regenerating adult rat dorsal root ganglion neurites follow the Schwann cell alignment present within EngNT (confocal micrographs of the same field showing neurons (red) after 3 days in co-culture with EngNT sheets formed using a rat Schwann cell line (green), scale bar 50 μm). The graph shows that a very high degree of alignment is achieved.

Experiment 2

EngNT Containing Schwann Cells Supports Nerve Regeneration In Vivo

Figure 4:
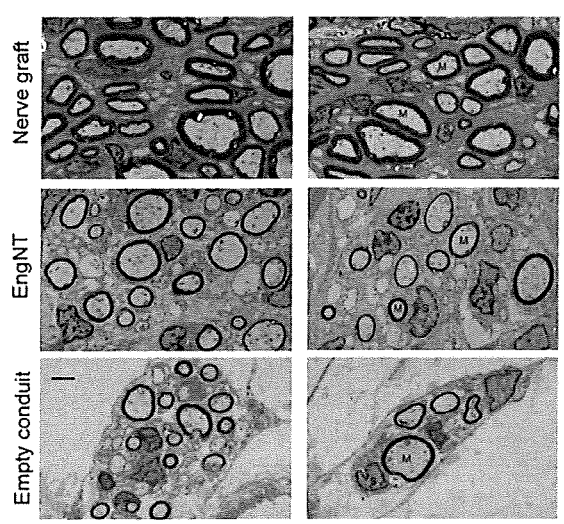
FIG. 4 shows transmission electron micrographs of a cross section at the midpoint of the repair site, 8 weeks after surgical repair of a 15 mm rat sciatic nerve gap.

FIG. 4 shows transmission electron micrographs of a cross section at the midpoint of the repair site, 8 weeks after surgical repair of a 15 mm rat sciatic nerve gap. Two rods of EngNT (made with a rat Schwann cell line) were used within NeuraWrap™ outer sheath. Controls were nerve grafts from littermates or empty NeuraWrap™ conduits.

Axon diameters, myelin G-ratio and regeneration density in the EngNT group were equivalent to the "gold standard" of nerve graft controls, and regeneration was superior to empty conduits.

Neural Stem Cell Tests

In addition to the rat Schwann cell line, other cell types have been tested; including bone marrow derived mesenchymal stem cells, differentiated adipose derived stem cells, ReNeuron's neural stem cell lines, both research grade ReNcell CX cells from Millipore and the clinical grade CTX cell line, data are shown in experiments 3 and 4. Differentiated CX and CTX (dCX, dCTX) cells in vitro supported and directed neurite outgrowth, with considerably better performance than was shown with adipose derived stem cells. Protocols for differentiation of CTX and CX cells are given above. When EngNT-dCX devices were implanted in animals they supported robust neuronal regeneration, showing ultrastructural features and myelination of the regenerated axons.

Preliminary experiments to investigate storage showed that cellular alignment in EngNT is retained after EngNT is frozen in liquid nitrogen and then thawed. Alignment was equivalent to untreated controls, with only 0.5±0.03% cell death.

Experiment 3

Figure 5:
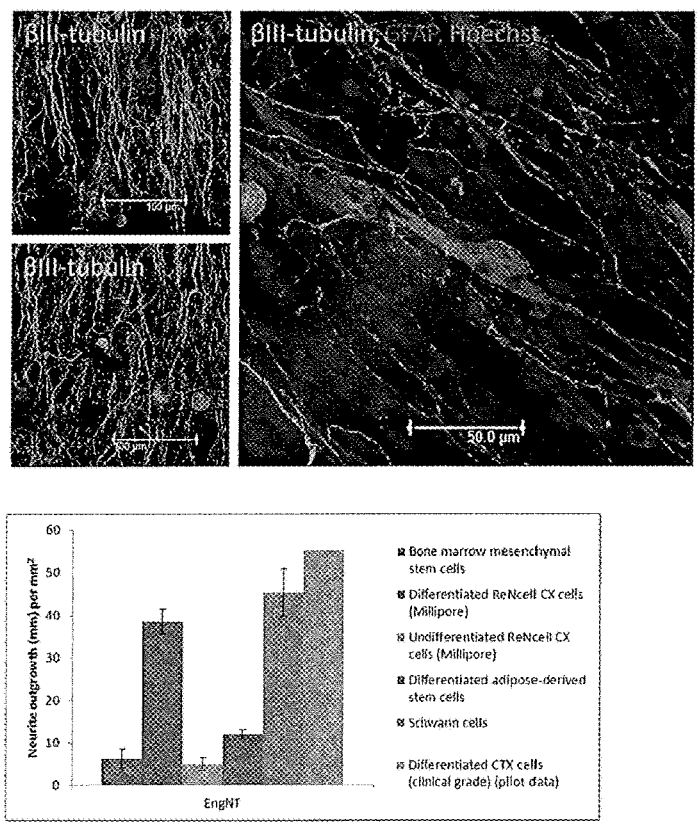
FIG. 5 shows the results of Experiment 3. EngNT made using differentiated ReNeuron CTX cells supports neurite growth in vitro and in vivo.

EngNT Made Using Differentiated ReNeuron CTX Cells Supports Neurite Growth In Vitro and In Vivo Results shown in FIG. 5. EngNT with aligned, differentiated ReNeuron cells (clinical grade CTX) supports and directs neurite outgrowth (green channel). Efficacy was assessed in vitro comparing cell types, and showed that EngNT with differentiated CTX cells supported neurite growth to a similar degree as with Schwann cells, and three-fold more growth was seen with dCTX than with differentiated adipose-derived stem cells.

Experiment 4

EngNT with ReNcell CX Cells (Millipore) Supports Regeneration In Vivo

Figure 6:
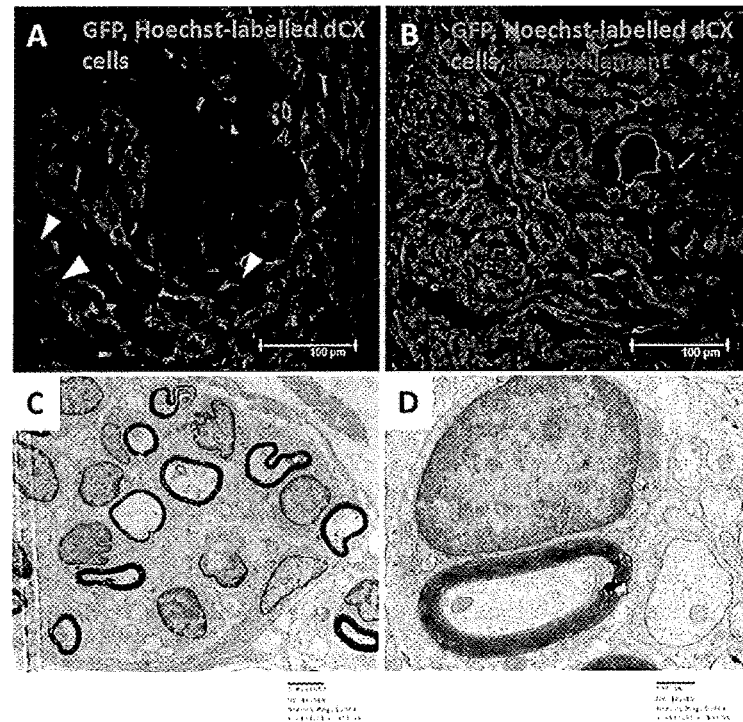
FIG. 6 shows the results of Experiment 4. EngNT with ReNcell CX cells (Millipore) supports regeneration in vivo. EngNT-dCX were labelled with Hoechst then implanted within an outer tube. (A) Hoechst-labelled dCX nuclei were present within the implanted device at 8 weeks, and were distinct from host GFP-labelled cells, indicating persistence of the dCX cells at the repair site. (B) The EngNT-dCX devices supported robust neuronal regeneration (red) and transmission electron micrographs (C and D) show ultrastuctural features and myelination of the regenerated axons.

Results shown in FIG. 6. EngNT-dCX were labelled with Hoechst then implanted within an outer tube. (A) Hoechst-labelled dCX nuclei were present within the implanted device at 8 weeks, and were distinct from host GFP-labelled cells, indicating persistence of the dCX cells at the repair site. (B) The EngNT-dCX devices supported robust neuronal regeneration (red) and transmission electron micrographs (C and D) show ultrastuctural features and myelination of the regenerated axons.

CONCLUSIONS

The data herein demonstrate that the tissue scaffold technology described herein can be used with cells other than Schwann cells, and in particular with neural stem cells. Such cells are available in therapeutic grade cells, and have been approved for therapeutic use. They also show broadly equivalent efficacy to the use of Schwann cells. This provides a new avenue for neural tissue repair strategies, which will not suffer from the same disadvantages as Schwann cells.

The present invention provides a number of advantages. In contrast to other tissue engineering approaches, the formation of the guide of the invention involves simply directing natural cell-matrix interactions in order to achieve a highly organized anisotropic structure, which is then stabilized by gentle removal of excess fluid to leave a final tissue-like construct. This avoids the need to manufacture elaborate porous or fibrillar scaffolds with surface modification to support cell attachment. Cells are distributed throughout the material from the outset thus avoiding the need for a cell-seeding step. The cell matrix interactions that shape the anisotropic structure occur naturally in tissue development and remodeling, avoiding the complex spatial and mechanical signals that arise when cells are forced to grow on stiff surfaces (such as within pores and channels or on the surfaces of fibers). Stabilisation of the material using the dehydrating (or plastic compression) process avoids the need for chemical cross-linking agents and retains the collagen in a native state suitable for integration with host tissue. Finally, the production process is appropriate for scale-up and automation.

The invention claimed is:

1. A method for producing an engineered tissue scaffold for neural repair, the method comprising:
   i) providing a cell guide comprising a hydrogel matrix seeded with neural stem cells obtained from a stable stem cell line, or with differentiated cells obtained from said stable stem cell line to form a seeded hydrogel matrix, the seeded hydrogel matrix being tethered at opposed first and second ends to a frame;
   ii) incubating the seeded hydrogel matrix in culture medium, whereby the neural stem cells or the differentiated cells generate tension within the seeded hydrogel matrix, such that the cells self-align within the seeded hydrogel matrix; and
   iii) removing liquid from the seeded hydrogel matrix in order to at least partially dehydrate the seeded hydrogel matrix to form a sheet while retaining cells within the seeded hydrogel matrix; thereby providing an engineered tissue scaffold.

2. The method of claim 1, wherein step i) comprises the steps of:
   i)a) providing a cell guide comprising a hydrogel matrix, and
   i)b) seeding the matrix with neural stem cells.

3. The method of claim 1, wherein the hydrogel matrix is a collagen matrix.

4. The method of claim 1, wherein the step of removing liquid from the seeded hydrogel matrix comprises contacting the seeded hydrogel matrix with an absorbent material.

5. The method of claim 1 wherein the method further comprises the step of iv) forming the sheet into a rod shape.

6. The method of claim 5, wherein the step of forming the sheet into a rod comprises rolling the sheet, or a portion of the sheet, to form a rod.

7. The method of claim 6, further comprising the step of encapsulating one or more sheets and/or rods in an outer sheath.

8. The method of claim 7 wherein the outer sheath is an at least partially dehydrated matrix without cells seeded within it.

9. The method of claim 1, further comprising the step of implanting the engineered tissue scaffold into a human or animal patient.

* * * * *